United States Patent
Morikawa et al.

(10) Patent No.: US 10,173,972 B2
(45) Date of Patent: Jan. 8, 2019

(54) METHOD FOR PRODUCING HIGH-PURITY AQUEOUS UREA SOLUTION IN UREA PRODUCTION PROCESS

(71) Applicant: TOYO ENGINEERING CORPORATION, Chiyoda-ku, Tokyo (JP)

(72) Inventors: Haruyuki Morikawa, Chiba (JP); Shuhei Nakamura, Chiba (JP); Keishi Sato, Chiba (JP)

(73) Assignee: TOYO ENGINEERING CORPORATION, Tokyo (JP)

( * ) Notice: Subject to any disclaimer, the term of this patent is extended or adjusted under 35 U.S.C. 154(b) by 0 days.

(21) Appl. No.: 15/508,994

(22) PCT Filed: Aug. 27, 2015

(86) PCT No.: PCT/JP2015/074200
§ 371 (c)(1),
(2) Date: Mar. 6, 2017

(87) PCT Pub. No.: WO2016/047356
PCT Pub. Date: Mar. 31, 2016

(65) Prior Publication Data
US 2017/0283372 A1    Oct. 5, 2017

(30) Foreign Application Priority Data
Sep. 22, 2014  (JP) ................. 2014-192989

(51) Int. Cl.
*C07C 273/16*    (2006.01)
*C07C 275/00*    (2006.01)
*C07C 273/04*    (2006.01)

(52) U.S. Cl.
CPC .......... *C07C 273/16* (2013.01); *C07C 273/04* (2013.01); *C07C 275/00* (2013.01); *C07B 2200/13* (2013.01)

(58) Field of Classification Search
None
See application file for complete search history.

(56) References Cited

U.S. PATENT DOCUMENTS

| 2,892,870 A | 6/1959 | Matile |
| 4,219,589 A * | 8/1980 | Niks ................ B01J 2/16 427/213 |
| 2008/0286188 A1* | 11/2008 | Meessen ............ B01D 53/79 423/365 |

FOREIGN PATENT DOCUMENTS

| CA | 649225 A | 9/1962 |
| CN | 102806011 A | 12/2012 |

(Continued)

OTHER PUBLICATIONS

PCT, International Search Report for PCT/JP2015/074200, dated Nov. 17, 2015.

(Continued)

*Primary Examiner* — Clinton A Brooks
(74) *Attorney, Agent, or Firm* — Orrick, Herrington & Sutcliffe LLP; Joseph A. Calvaruso (57) ABSTRACT

The present invention relates to a method for producing a high-purity aqueous urea solution, utilizing a urea production process at least including a urea synthesis step of synthesizing urea from a raw material feed to produce a urea synthesis liquid, and a urea purification step of purifying the urea synthesis liquid to produce an aqueous urea solution with high urea concentration. The present invention includes a urea crystallization step of separating a part of the urea synthesis liquid and/or a part of the aqueous urea solution and crystallizing urea contained in the separated urea syn- (Continued)

thesis liquid and/or aqueous urea solution to produce solid crystal urea, and a mixing step of mixing the crystal urea with water to produce a high-purity aqueous urea solution. A high-purity aqueous urea solution to be produced is an aqueous urea solution with high purity suitable as a reducing agent for SCR.

7 Claims, 3 Drawing Sheets

(56) References Cited

FOREIGN PATENT DOCUMENTS

| | | |
|---|---|---|
| DE | 1618926 B1 | 1/1971 |
| JP | 2008-239574 A | 10/2008 |
| JP | 2008-538133 A | 10/2008 |
| JP | 2008-280263 A | 11/2008 |
| WO | WO 2013/055219 A1 | 4/2013 |

OTHER PUBLICATIONS

EP, Extended Search Report for EP application No. 15844606.2, dated Feb. 28, 2018.

* cited by examiner

METHOD FOR PRODUCING HIGH-PURITY AQUEOUS UREA SOLUTION IN UREA PRODUCTION PROCESS

TECHNICAL FIELD

The present invention relates to a method for producing a high-purity aqueous urea solution. In particular, it relates to a method for producing a high-purity aqueous urea solution, utilizing a part of a produced aqueous urea solution as a precursor in a urea production process (urea production plant).

BACKGROUND ART

As a method for reducing and purifying NOx in exhaust gas from an internal-combustion engine such as a diesel engine, there is suggested a method that utilizes a catalytic converter of a selective catalytic reduction system (SCR system) in which urea water is applied. The urea SCR system is a system that uses urea water as a reducing agent to mix the agent in an exhaust gas, thereby purifying the exhaust gas with an SCR catalytic converter. In the system, urea changes into ammonia in the exhaust gas, and NOx in the exhaust gas is linked with the ammonia in the SCR catalytic converter to be decomposed into water and nitrogen, and, therefore, the system is considered to be a promising technique for making exhaust gas clean.

Further, standardization about purity of an aqueous urea solution for use in a urea SCR system is under study. For example, German Institute for Standardization/Deutsche Industrie Normen (DIN) 70070 prescribes an aqueous urea solution for an in-vehicle SCR catalytic converter for diesel cars. In the standard, a 32.5% aqueous urea solution is prescribed. Meanwhile, in the present invention, hereinafter, an aqueous urea solution with high purity suitable as a reducing agent for an SCR application and the like is called a "high-purity aqueous urea solution."

As a method for producing a high-purity aqueous urea solution, there is known a method for dissolving commercially available urea for fertilizer in purified water to form an aqueous solution. The production method is a comparatively simple method. However, generally, commercially available urea contains aldehyde, an anticaking additive, a coating agent and the like. These aldehyde, anticaking additive, coating agent and the like correspond to impurities for an aqueous urea solution for SCR. Therefore, in a conventional method for producing a high-purity aqueous urea solution, it is necessary to remove impurities from commercially available urea for fertilizer. Accordingly, the conventional method for producing a high-purity aqueous urea solution is not an effective method. Further, when the production method is to be utilized, it is necessary to pay attention also to acquisition of a raw material.

Consequently, it is tried to obtain a high-purity aqueous urea solution in a stage prior to production of urea corresponding to a "finished product" such as urea for fertilizer, that is, in a urea production process. For example, in PTL 1, there is suggested a method for partially separating an aqueous urea solution (UREA-COMPRISING AQUEOUS STREAM) produced in a urea production process, and diluting the aqueous urea solution with water to produce an aqueous urea solution of 30 to 35% by weight.

CITATION LIST

Patent Literature

PTL 1: Published Japanese translation of PCT patent application No. 2008-538133 (PCT/NL 2006/000097)

SUMMARY OF INVENTION

Technical Problem

The method for producing an aqueous urea solution described in the PTL 1 dilutes an aqueous urea solution after urea synthesis and before finishing. Accordingly, by use of the production method, there can be produced a high-purity aqueous urea solution not containing impurities such as aldehyde. However, in the method described in PTL 1, although additive impurities such as aldehyde do not exist, occasionally ammonia, which is an unreacted component in the synthesis, is contained. Since ammonia also corresponds to an impurity in the standard of a reducing agent for SCR, removal of ammonia becomes necessary.

Further, with a conventional technique in PTL 1, there is a problem more troublesome than the removal of impurities such as ammonia. The problem is how to handle biuret ($C_2H_5N_3O_2$: dimer of urea) that may be contained in an aqueous urea solution after a synthesis step. Biuret is also regulated in concentration in the standard of a high-purity aqueous urea solution for SCR, and must be suppressed to a certain amount or less. However, biuret is not a general impurity having a different chemical composition, and therefore, the separation is difficult. Consequently, once generated biuret exists with urea after a synthesis step in a urea production process.

Furthermore, an additional problem of biuret also exists in addition to the difficulty of separation from an aqueous urea solution. The additional problem is that the generated quantity of biuret changes according to operation conditions of a plant, even if the urea production plant is the same. The additional problem will be described in detail below.

Biuret is generated by heating a urea synthesis liquid or an aqueous urea solution after a urea synthesis step at high temperatures, and a generated quantity becomes larger as an operation time at high temperatures becomes longer. In a general urea plant, a process design and an equipment design are performed based on a design production quantity, and the optimum operation condition is set. Furthermore, under the optimum condition, the influence of the problem of biuret is small. However, due to a shortage of a raw material, performance deterioration of equipment or the like, a situation is not uncommon in which the operation needs to be performed at a production quantity lower than the design production quantity. Under an operation condition of a low production quantity, retention time of a urea synthesis liquid or an aqueous urea solution in equipment increases. The increase in the retention time brings about a state in which biuret is generated easily. Accordingly, even if a plant generates a small quantity of biuret in an aqueous urea solution under an operation condition for a design production quantity, biuret might be generated excessively as a result of the change in the operation condition.

The conventional method for producing a high-purity aqueous urea solution having been described cannot cope with the increase in a biuret concentration due to the change in an operation condition. The present invention provides a method for producing a high-purity aqueous urea solution suitable as a reducing agent for SCR in a urea production plant. The method utilizes an aqueous urea solution after urea synthesis in the urea production plant for production of a high-purity aqueous urea solution. Furthermore, the method can produce a high-purity aqueous urea solution containing a small quantity of impurities and biuret. Here, concrete indicators of a high-purity aqueous urea solution in the present invention is that urea concentration is 32 to 33% by mass in an aqueous urea solution, biuret concentration is not more than 0.2% by mass, and concentration of impurities other than urea/water is not more than 0.4% by mass.

Solution to Problem

The present invention that solves the above-mentioned problem is a method for producing a high-purity aqueous urea solution in a urea production process, the process including at least a urea synthesis step for synthesizing urea from a raw material feed to produce a urea synthesis liquid and a urea purification step for purifying the urea synthesis liquid to produce an aqueous urea solution having high urea concentration, the method including: a urea crystallization step of separating a part of the urea synthesis liquid and/or a part of the aqueous urea solution, and crystallizing urea contained in a separated urea synthesis liquid and/or aqueous urea solution to produce crystal urea being a solid; and a mixing step of mixing the crystal urea with water to produce a high-purity aqueous urea solution.

The present invention includes partially separates at least either a urea synthesis liquid or an aqueous urea solution each produced in two steps of a urea synthesis step and a urea purification step, which a general urea production process includes at the minimum. At least either the separated urea synthesis liquid or the separated aqueous urea solution is crystallized to produce solid crystal urea. Further, it is characterized in that the produced crystal urea is mixed and dissolved in water as a precursor to produce a high-purity aqueous urea solution suitable as a reducing agent for SCR.

Hereinafter, the method for producing a high-purity aqueous urea solution according to the present invention will be described. A urea production process to which the present invention is applied is a general urea production process. As general urea production processes, commercially known are processes based on known urea production technologies such as a complete circulation process and stripping process. The general urea production process includes, as indispensable steps, two steps which are a urea synthesis step of synthesizing urea from a raw material feed to produce a urea synthesis liquid, and a urea purification step of purifying the urea synthesis liquid to produce an aqueous urea solution. Further, as steps which are appropriately added to these steps, there are included a recovery step of collecting unreacted materials separated in the urea purification step, a urea concentrating step of concentrating the aqueous urea solution from the urea purification step up to concentration necessary for finishing, and a finishing step of forming the concentrated aqueous urea solution into a finished product such as prilled urea. Hereinafter, the present invention will be described with description of respective steps.

In the urea synthesis step, urea is synthesized from ammonia and carbon dioxide which are raw materials under a high temperature (175 to 200° C.) and high pressure (130 to 200 kg/cm$^2$G) condition. A urea synthesis liquid from the urea synthesis step includes urea, ammonium carbamate as an unreacted material, ammonia, water and the like. Such a urea synthesis liquid is purified in the urea purification step. In the urea purification step, ammonium carbamate is decomposed into ammonia and carbon dioxide by heating of the urea synthesis liquid under reduced pressure from synthesis pressure, and ammonia and carbon dioxide are separated and purified from the urea synthesis liquid to form an aqueous urea solution.

Obtained is an aqueous urea solution containing a minute amount of ammonia and carbon dioxide from the urea purification step. The aqueous urea solution is sent to the urea concentrating step. In the urea concentrating step, the aqueous urea solution is heated in a vacuum state and concentrated up to concentration necessary for the finishing step. Generally, it is concentrated up to about 99.7% for production of prilled urea, and up to 96 to 98% for production of granular urea. The concentrated aqueous urea solution is formed into prilled urea, granular urea or the like in the finishing step, which are then shipped to markets. Meanwhile, ammonia and carbon dioxide separated from an aqueous urea solution in the urea purification step are sent to the recovery step. In the recovery step, ammonia and carbon dioxide are dissolved in water and then condensed. The condensed water is sent back to the urea synthesis step as a recovered liquid and utilized for urea synthesis.

In contrast to the above-described general urea production process, the present invention draws and separates a part of a urea synthesis liquid from the urea synthesis step or an aqueous urea solution from the urea purification step, or a part of both of these solutions. Then, the urea synthesis liquid and/or aqueous urea solution is crystallized to produce solid crystal urea. Timing at which a part of the solution containing urea (urea synthesis liquid and/or aqueous urea solution) is separated targets preferably an aqueous urea solution in or after the urea purification step. Because, the urea synthesis liquid contains ammonium carbamate or ammonia in high concentration, and therefore, the utilization of the urea synthesis liquid might affect a crystallization process. An aqueous urea solution from the urea purification step contains a small quantity of ammonium carbamate and ammonia, and therefore, it is suitable as an object for a crystallization treatment.

When a part of an aqueous urea solution from the urea purification step is separated, an aqueous urea solution directly after the urea purification step may be separated, or a subsequent aqueous urea solution may be separated. For example, as to a urea production process having the above-described urea concentrating step, a part of an aqueous urea solution between the urea purification step and the urea concentrating step may be separated. Further, a part of an aqueous urea solution in the urea concentrating step may be separated. Furthermore, both of the aqueous urea solutions may be separated.

The present invention sets a partially separated urea synthesis liquid and/or aqueous urea solution as an object, and crystallizes urea contained in the urea synthesis liquid and/or aqueous urea solution in the urea crystallization step. Concrete treatment contents in the urea crystallization step include a treatment of first, heating the partially separated urea synthesis liquid and/or aqueous urea solution to evaporate water, while suppressing the generation of biuret. The treatment includes a step of generating slurry containing crystal urea. The generated slurry includes solid urea crystals dispersed in the aqueous urea solution. The urea crystallization step further includes a step of subjecting the slurry to solid-liquid separation into crystal urea and a mother liquid. Hereby, urea crystals are collected.

Slurrying of the urea synthesis liquid and/or aqueous urea solution in the urea crystallization step is performed with a crystal generation apparatus such as a crystallization tank (crystallization tower), a crystallizing tank or crystallizer. Treatment conditions for generating slurry preferably include pressure and temperature, at which the urea synthesis liquid and/or aqueous urea solution can be heated in vacuum at relatively low temperatures to crystallize urea. Concrete treatment conditions preferably include heating the aqueous urea solution at 60 to 80 mmHg (abs.) in pressure and 50 to 80° C. in temperature. It is possible to evaporate water and to obtain crystal urea by heating under such conditions while suppressing decomposition of urea and generation of biuret in the solution. As a consequence of the treatment, urea is crystallized to generate slurry composed of solid crystal urea and the aqueous urea solution. In a step of generating slurry by the crystallization, it is preferable to perform the treatment until the crystal urea concentration (crystal urea/(crystal urea+urea in aqueous solution)) becomes 20 to 45% by mass.

Then, the slurry thus generated is subjected to solid-liquid separation to give solid crystal urea. As to concrete methods of solid-liquid separation, those by a filtering device, a centrifugal separator and the like are preferable. Meanwhile, it is unnecessary to make crystal urea be in a completely dried state containing no moisture. Crystal urea after a solid-liquid separation may contain moisture in around 1 to 3% by mass.

Moreover, a mother liquid obtained with crystal urea by a solid-liquid separation is water containing urea (aqueous urea solution). The mother liquid after a solid-liquid separation can be circulated into a crystal generation apparatus for generating slurry and be retreated. Further, it may be treated as a waste liquid without circulation into the crystal generation apparatus.

Incidentally, as described above, in an ordinary urea production process, there may be such a case that a biuret amount contained in a urea synthesis liquid from the urea synthesis step or contained in an aqueous urea solution from the urea purification step increases due to a change in operation conditions such as lowering of an operation load. In this case, it is estimated that biuret concentration in a mother liquid of slurry generated in the urea crystallization step also increases. Then, since crystal urea after a solid-liquid separation in the urea crystallization step is accompanied with a minute amount of mother liquid of slurry, obtained crystal urea might be not suitable for production of a high-purity aqueous urea solution.

In the present invention, there is devised a countermeasure for the probability of increase in a biuret amount in an aqueous urea solution as described above. The countermeasure is to make it possible to send back, to the urea synthesis step, a part of a mother liquid obtained by a solid-liquid separation of slurry generated in the urea crystallization step. As described above, it is possible to lower the biuret amount in the mother liquid and to reduce an amount of biuret accompanying crystal urea after a final solid-liquid separation, by returning a part of the mother liquid to the urea synthesis step. Biuret contained in the mother liquid sent back to the urea synthesis step is in a state of reaction equilibration in a reactor in the urea synthesis step, and therefore, it changes to urea reversibly.

When a part of the mother liquid is to be sent back as described above, the mother liquid may be sent directly from the urea crystallization step to the urea synthesis step. Further, when a urea production process has a recovery step, the mother liquid may be sent back to the recovery step and the mother liquid may be sent back to the urea synthesis step with a recovered liquid from the recovery step. It is possible to dissolve ammonia/carbon dioxide separated in the urea purification step in the mother liquid, by sending back the mother liquid to the recovery step. Hereby, an amount of an absorption solvent (water) sent to the recovery step can be decreased. As a consequence of the reduction of the amount of an absorption solvent, water decreases in a recovered liquid to be returned to the urea synthesis step. The decrease in water in a recovered liquid is favorable for a urea synthesis reaction, and there is such an advantage that a synthesis ratio of urea can be improved from relation of a urea synthesis equilibrium.

However, it is not always necessary to perform a partial recycle of a mother liquid after subjecting slurry to a solid-liquid separation, which is described above. It is preferable to dispose a line from the urea crystallization step to the recovery step or the urea synthesis step in a urea production plant so that a partial recycle of a mother liquid can be performed selectively and optionally.

The present invention mixes solid crystal urea obtained in the above-described urea crystallization step with water to produce a high-purity aqueous urea solution. A general mixing apparatus such as a mixing tank can be applied to the production of an aqueous urea solution by the mixing step. Heat necessary for dissolving urea can be supplied by steam heating or hot water, and a high-purity aqueous urea solution is produced while urea concentration and temperature are being adjusted.

Meanwhile, as a criterion when crystal urea is dissolved in water, DIN 70070 is mentioned, which is the standard for an aqueous urea solution for an SCR reducing agent. The constitution of an aqueous solution in the standard is as follows. An amount of water to be mixed when an aqueous urea solution is produced can be calculated so as to give following urea concentration, in consideration of the amount of crystal urea and the amount of contained moisture.

Urea concentration: 31.8% by mass (min.) to 33.2% by mass (max.)
Alkalinity (in terms of ammonia): 0.2% by mass max.
Biuret concentration: 0.3% by mass max.
Aldehyde: 5 mg/kg max.
Insoluble matters: 20 mg/kg max.
Phosphorous (in terms of phosphoric acid), calcium, iron: each 0.5 mg/kg max.
Copper, zinc, chromium, nickel, magnesium, sodium, potassium: each 0.2 mg/kg max.

Advantageous Effects of Invention

As described hereinbefore, according to the present invention, there can be produced an aqueous urea solution with high purity suitable as a reducing agent for SCR in a urea production plant. According to the present invention, there can be produced an aqueous urea solution with a small amount of impurities and biuret. The present invention can cope with a change in operation conditions of a urea production plant and the like, and can produce stably a high-purity aqueous urea solution.

MODE FOR CARRYING OUT THE INVENTION

Figure 1:
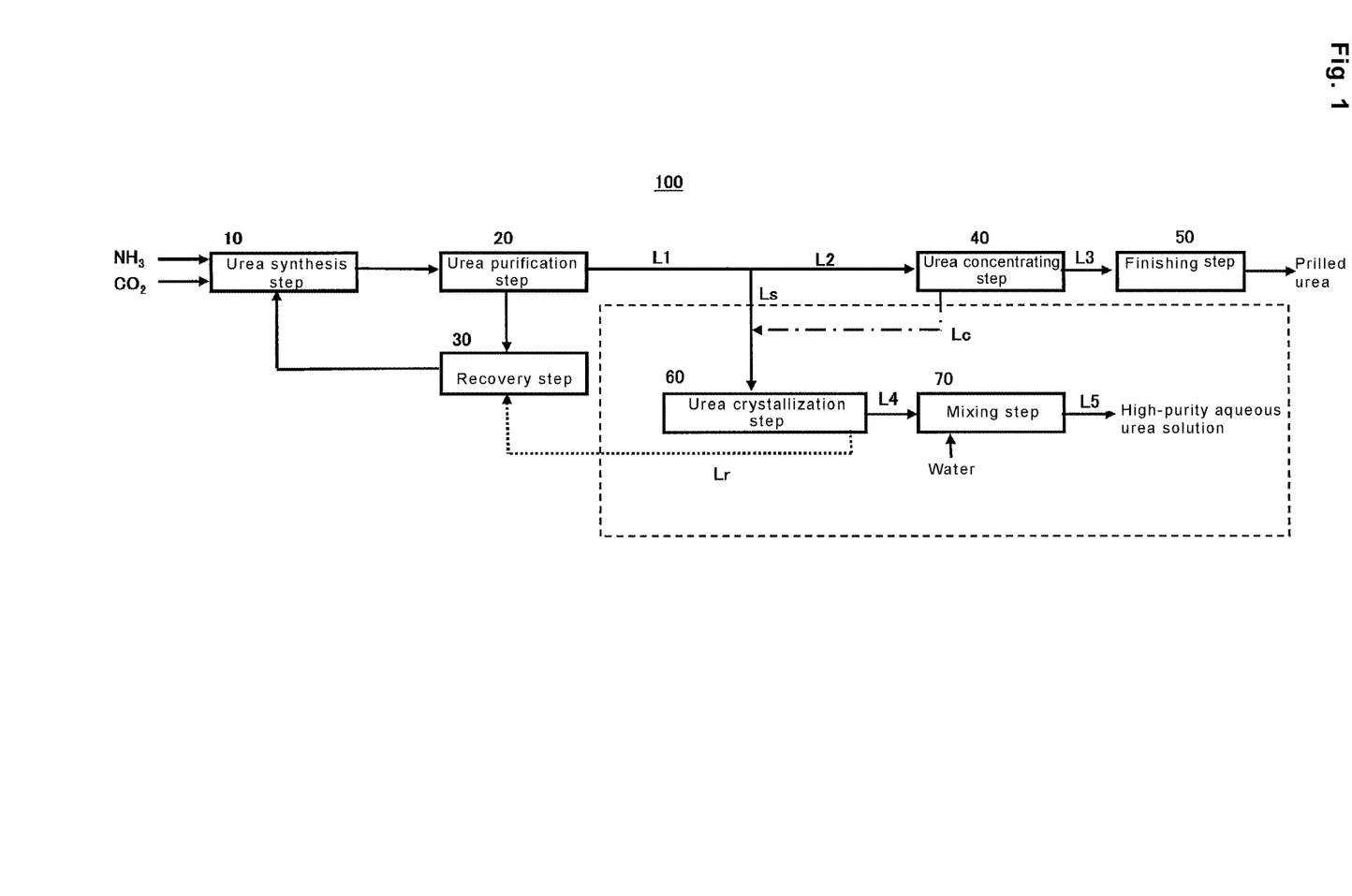
FIG. 1 shows a configuration of a urea production process according to the present embodiment.

Embodiments of the present invention will be described based on Examples described below. FIG. 1 illustrates respective steps in a urea production process 100 including a method for producing an aqueous urea solution according to the present embodiment. In FIG. 1, the urea production process 100 includes a urea synthesis step 10, a urea purification step 20, a recovery step 30, a urea concentrating step 40, and a finishing step 50. Respective steps are systematized by piping lines (L1 to L5).

Further, the urea production process 100 according to the present embodiment is configured to be able to separate and draw a part of an aqueous urea solution from the urea purification step 20. In the present embodiment, a line (Ls) between the urea purification step 20 and the urea concentrating step 40 is branched. Further, there is also set a line (Lc) for enabling separation of a part of an aqueous urea solution in the urea concentrating step 40.

Furthermore, the urea production process 100 according to the present embodiment includes a urea crystallization step 60 and a mixing step 70 for mixing crystal urea produced in the urea crystallization step 60 with water to produce a high-purity aqueous urea solution.

The urea crystallization step 60 includes a step of concentrating an aqueous urea solution from the urea purification step 20 by evaporating water with heating and generating slurry by depositing crystal urea with temperature lowered in vacuum. Further, it includes a step of subjecting the slurry to solid-liquid separation. The solid crystal urea subjected to the solid-liquid separation in the urea crystallization step 60 is mixed with water in the mixing step 70 to produce a high-purity aqueous urea solution.

Further, to the urea crystallization step 60, there is set a line (Lr) for sending back, to the recovery step 30, at least a part of a mother liquid obtained by subjecting the slurry to the solid-liquid separation. The opening and closing of the line Lr is controlled with a control valve or the like, and can be performed according to an operation state, biuret concentration in an aqueous urea solution or the like.

The above-described urea production process 100 according to the present embodiment can be practiced by a urea production plant composed of a group of apparatuses for practicing respective steps. The urea production plant includes a urea synthesis apparatus for the urea synthesis step 10, a urea purification apparatus for the urea purification step 20, a collection apparatus for the recovery step 30, a urea concentrating apparatus for the urea concentrating step 40, and a finishing apparatus for the finishing step 50. Further, it includes a urea crystallization apparatus for the urea crystallization step 60 and a mixing apparatus for mixing crystal urea with water to produce a high-purity aqueous urea solution. The urea crystallization apparatus has, as main equipment, a crystallization tank for depositing crystal urea from an aqueous urea solution and a centrifugal separator for solid-liquid separation. Moreover, the mixing apparatus has a mixing tank as main equipment. These apparatuses are usually configured with a plurality of equipment such as plural towers and tanks, heat exchangers, pumps and auxiliaries. The configuration is the same as that of a general urea production plant, and no particularly new one is required. In addition, these apparatuses may be configured with single equipment alone.

In the present embodiment, material balances under two operation states were obtained for the above urea production process. Meanwhile, material balances shown in Examples and Comparative Examples below are those based on an apparatus for which a prilled urea production capacity of 1725 ton/day is set as a design production volume of a urea production plant.

EXAMPLE 1

In this example, there will be described a material balance in a case of producing a high-purity aqueous urea solution while operating a prilled urea production plant under ordinary operation conditions based on a design production volume. Tables 1 and 2 show compositions of feed in respective lines in and after the urea purification step 20.

The urea synthesis step 10 having received a raw material feed supply of ammonia and carbon dioxide generates a urea synthesis liquid. As to the urea synthesis liquid containing urea, ammonium carbamate, ammonia and water as main components, ammonium carbamate is decomposed, and ammonia and carbon dioxide are separated from the urea synthesis liquid to form an aqueous urea solution, in the urea purification step 20. The aqueous urea solution from the urea purification step 20 (line L1) is an aqueous urea solution containing a minute amount of ammonia and carbon dioxide, and, in the present example, it was an aqueous urea solution of 0.33% by mass in biuret concentration. The composition of the aqueous urea solution in the line L1 is as listed in Table 1.

A part of the aqueous urea solution from the urea purification step 20 is drawn for the urea crystallization step (line Ls). On the other hand, the remaining aqueous urea solution is sent to the urea concentrating step 40 (line L2).

The aqueous urea solution sent to the urea concentrating step 40 by the line L2 is heated and concentrated in vacuum. On this occasion, usually a molten urea liquid is obtained generally under two-stage operation conditions of 150 to 250 mmHg (abs.) and 25 to 30 mmHg (abs.) in pressure and 125 to 140° C. in heating temperature. Moreover, in the concentrating step, ammonia and carbon dioxide in the aqueous urea solution were drawn as gas, and were separated and collected with ammonia and carbon dioxide generated as a result of hydrolysis of a part of urea. In the present example, a urea solution was concentrated up to about 99.7%. Then, the concentrated urea liquid is sprayed in a shower-like state from an upper part, and is solidified and cooled by the contact with the air rising from a lower part to generate a prilled urea product, in the finishing step.

A part of the aqueous urea solution from the urea purification step 20 is introduced to a crystallizing tank in the urea crystallization step 60 by the line Ls branched from the line L1. The crystallizing tank was operated in vacuum of 75 mmHg (abs.) at 60° C. to generate crystal urea. Ammonia and carbon dioxide in the aqueous urea solution are separated with water and urea being a minute amount of mist in the crystallizing tank (accordingly, a urea amount in slurry after purification of crystal is reduced slightly). Subsequently, solid-liquid separation was performed with a centrifugal separator to give crystal urea (line L4). Meanwhile, a mother liquid obtained by separating crystal urea from slurry is sent back to a crystallization tank. In Example 1, a part of the mother liquid separated from slurry is not sent back to the recovery step. It is configured so that all urea introduced to the urea crystallization step 60 via the line Ls is converted to crystal urea.

The generated crystal urea was sent to the mixing step 70, in which water (8334 kg/h) was added and the crystal urea was dissolved with heating to produce a high-purity aqueous urea solution.

There are listed, in Table 1, material balances of the lines L1, L2, and L3 from the urea purification step 20 until prilled urea is produced in the finishing step, and there are listed, in Table 2, material balances of the lines Ls, L4, and L5 until the high-purity aqueous urea solution is produced.

TABLE 1

|  | L1 | L2 | L3 |
|---|---|---|---|
| Urea | 72227 kg/h | 68156 kg/h | 67145 kg/h |
| Biuret | 352 kg/h | 332 kg/h | 543 kg/h |
| Biuret concentration | 0.33 wt % | 0.33 wt % | 0.8 wt % |
| Ammonia | 582 kg/h | 549 kg/h | — |
| Carbon dioxide | 341 kg/h | 322 kg/h | — |
| Water | 33725 kg/h | 31824 kg/h | 136 kg/h |
| Total | 107227 kg/h | 101183 kg/h | 67823 kg/h |

TABLE 2

|  | Ls | L4 | L5 |
|---|---|---|---|
| Urea | 4072 kg/h | 4063 kg/h | 4063 kg/h |
| Biuret | 20 kg/h | 20 kg/h | 20 kg/h |
| Biuret concentration | 0.33 wt % | 0.48 wt % | 0.16 wt % |
| Ammonia | 33 kg/h | — | — |
| Carbon dioxide | 19 kg/h | — | — |
| Water | 1901 kg/h | 83 kg/h | 8417 kg/h |
| Total | 6044 kg/h | 4166 kg/h | 12500 kg/h |

From Table 2, it is known that a high-purity aqueous urea solution having a biuret concentration of 0.16% by mass can be produced in the present example. On the other hand, prilled urea produced from the urea concentrating step 40 via the finishing step 50 has biuret concentration of 0.8% by mass, and thus the biuret concentration increases relative to that in the aqueous urea solution from the urea purification step 20. This is because, in the treatment in or after the urea concentrating step, biuret is additionally generated by a partial dimerization of urea with the previous biuret left as it is. However, with regard to this example, the biuret concentration in the produced prilled urea is not so high, and therefore it is possible to produce a high-purity aqueous urea solution even by diluting the produced prilled urea.

EXAMPLE 2

This example assumes a case where a production volume of prilled urea lowers due to a shortage of a raw material in the same urea production plant as in Example 1. In this example, the aqueous urea solution (L1) from the urea purification step 20 was partially separated (Ls) so that the production volume of a high-purity aqueous urea solution was equal to that in Example 1. Then, prilled urea was produced from a remaining aqueous urea solution (L2).

In this example, too, slurry was generated in the urea crystallization step 60, and a mother liquid after solid-liquid separation is sent back to the crystallization tank. However, in this example, a part of the mother liquid is sent back to the recovery step 30 by the line Lr so that it is finally recycled in the urea synthesis step 10.

There are listed in Table 3 material balances in lines L1, L2, and L3 from the urea purification step 20 up to the production of prilled urea in the finishing step, and there are listed in Table 4 material balances in lines Ls, Lr, L4, and L5 up to the production of a high-purity aqueous urea solution, in Example 2. Meanwhile, operation conditions in the urea synthesis step 10, the urea purification step 20, the urea concentrating step 40 and the finishing step 50 in Example 2 are the same as in Example 1. Further, operation conditions of the crystallizing tank in the urea crystallization step 60 are also the same as in Example 1 (75 mmHg (abs.), 60° C.).

TABLE 3

|  | L1 | L2 | L3 |
|---|---|---|---|
| Urea | 41871 kg/h | 37618 kg/h | 36989 kg/h |
| Biuret | 251 kg/h | 226 kg/h | 412 kg/h |
| Biuret concentration | 0.4 wt % | 0.4 wt % | 1.1 wt % |
| Ammonia | 337 kg/h | 303 kg/h | — |
| Carbon dioxide | 198 kg/h | 178 kg/h | — |
| Water | 19551 kg/h | 17565 kg/h | 83 kg/h |
| Total | 62208 kg/h | 55896 kg/h | 37484 kg/h |

TABLE 4

|  | Ls | Lr | L4 | L5 |
|---|---|---|---|---|
| Urea | 4253 kg/h | 181 kg/h | 4063 kg/h | 4063 kg/h |
| Biuret | 26 kg/h | 9 kg/h | 17 kg/h | 17 kg/h |
| Biuret concentration | 0.43 wt % | 3.55 wt % | 0.4 wt % | 0.13 wt % |
| Ammonia | 34 kg/h | — | — | — |
| Carbon dioxide | 20 kg/h | — | — | — |
| Water | 1901 kg/h | 63 kg/h | 82 kg/h | 8421 kg/h |
| Total | 6044 kg/h | 253 kg/h | 4162 kg/h | 12500 kg/h |

In the case of Example 2, volumes of fluids flowing in respective steps lower due to the lowering of the production volume. However, the size of each equipment is designed so that prilled urea of a design production volume (1725 ton/day) can be produced. Consequently, retention times of a urea synthesis liquid and aqueous urea solution in respective steps increase, and thereby the generation amount of biuret will increase. With reference to Table 3, the biuret concentration of the aqueous urea solution (L1) from the urea purification step 20 is 0.4% by mass. The biuret concentration is slightly higher than that in Example 1.

The aqueous urea solution was partially drawn (Ls), and crystal urea was deposited and separated in the crystallizing tank in the urea crystallization step 60 to generate slurry. Solid-liquid separation was performed with a centrifugal separator to give crystal urea (L4). As to the mother liquid from the centrifugal separator obtained at that time, a part of the mother liquid was sent to the recovery step (Lr), and the rest was returned to the crystallization tank. Further, 8338 kg/h of water was added to the crystal urea from L4 in the mixing step 70, which was heated to produce a high-purity aqueous urea solution. The biuret concentration of the aqueous urea solution was 0.13% by mass, which falls within the standard of a high-purity aqueous urea solution for an SCR reducing agent.

On the other hand, the remaining part (L2) of the aqueous urea solution from the urea purification step 20 was concentrated (L3) in the urea concentrating step 40 to produce prilled urea. The biuret concentration of the prilled urea is 1.1% by mass. When the prilled urea is dissolved in water to produce a high-purity aqueous urea solution, about 112000 kg/h of water is required. Then, the biuret concentration of an aqueous urea solution to be produced is 0.36% by mass, which falls outside the standard. As described above, in Example 2, the biuret concentration increased in the aqueous urea solution due to the lowering of the operation load. As the result, the produced prilled urea was inadequate for a raw material of an aqueous urea solution for an SCR reducing agent. In this way, in Example 2, a high-purity aqueous urea solution within the standard was not able to be produced from prilled urea being a finished product. However, in this example, it was confirmed that a high-purity aqueous urea solution within the standard was able to be produced by utilization of crystal urea obtained by partially drawing and treating an aqueous urea solution.

REFERENCE EXAMPLE

A result of a case was examined where the mother liquid of slurry generated in the urea crystallization step 60 was not sent back to the recovery step 30 in Example 2 (a case where line Lr was closed).

The Reference Example assumes a case where a prilled urea production volume lowers due to a shortage of a raw material, as in Example 2. Further, the aqueous urea solution (L1) from the urea purification step 20 was partially separated (Ls) so that the production volume of a high-purity aqueous urea solution was equal to that in Example 1. Furthermore, in the urea crystallization step 60, all urea, which was introduced by returning, to the crystallization tank, a part of the mother liquid obtained from generated slurry by solid-liquid separation without sending it back to the recovery step, was formed into crystal urea. Further, prilled urea was produced from the aqueous urea solution (L2) being the residue of L1. There are listed in Table 5 material balances in lines L1, L2, and L3, and there are listed in Table 6 material balances in lines Ls, Lr, L4, and L5 in the Reference Example.

TABLE 5

|  | L1 | L2 | L3 |
|---|---|---|---|
| Urea | 41871 kg/h | 37799 kg/h | 37170 kg/h |
| Biuret | 251 kg/h | 225 kg/h | 412 kg/h |
| Biuret concentration | 0.4 wt % | 0.4 wt % | 1.1 wt % |
| Ammonia | 337 kg/h | 304 kg/h | — |
| Carbon dioxide | 198 kg/h | 179 kg/h | — |
| Water | 19551 kg/h | 17650 kg/h | 83 kg/h |
| Total | 62208 kg/h | 56157 kg/h | 37665 kg/h |

TABLE 6

|  | Ls | Lr | L4 | L5 |
|---|---|---|---|---|
| Urea | 4072 kg/h | Without recycling | 4063 kg/h | 4063 kg/h |
| Biuret | 26 kg/h |  | 26 kg/h | 26 kg/h |
| Biuret concentration | 0.43 wt % |  | 0.62 wt % | 0.21 wt % |
| Ammonia | 33 kg/h |  | — | — |
| Carbon dioxide | 19 kg/h |  | — | — |
| Water | 1901 kg/h |  | 83 kg/h | 8411 kg/h |
| Total | 6051 kg/h | — | 4172 kg/h | 12500 kg/h |

From Table 6, the biuret concentration in the high-purity aqueous urea solution (L5) produced in the Reference Example becomes higher than those in Examples 1 and 2. This is because the biuret concentration in the aqueous urea solution L1 is high due to the lowering of an operation load. In the case of the Reference Example, the biuret concentration satisfies the reference value at least. However, it is considered that, when a case is assumed where the biuret concentration in an aqueous urea solution becomes higher, a high-purity aqueous urea solution to be produced in the case may not satisfy the standard. Further, in the Reference Example as in Example 2, a suitable high-purity aqueous urea solution cannot be produced from the prilled urea being the finished product. Accordingly, it is preferable to allow a part of mother liquid of slurry to be recycled selectively and optionally, assuming a change in operation conditions.

Next, there was examined a conventional urea production plant without setting of the urea crystallization step 60 with respect to the urea production plant according to the present embodiment described above.

COMPARATIVE EXAMPLE 1

Figure 2:
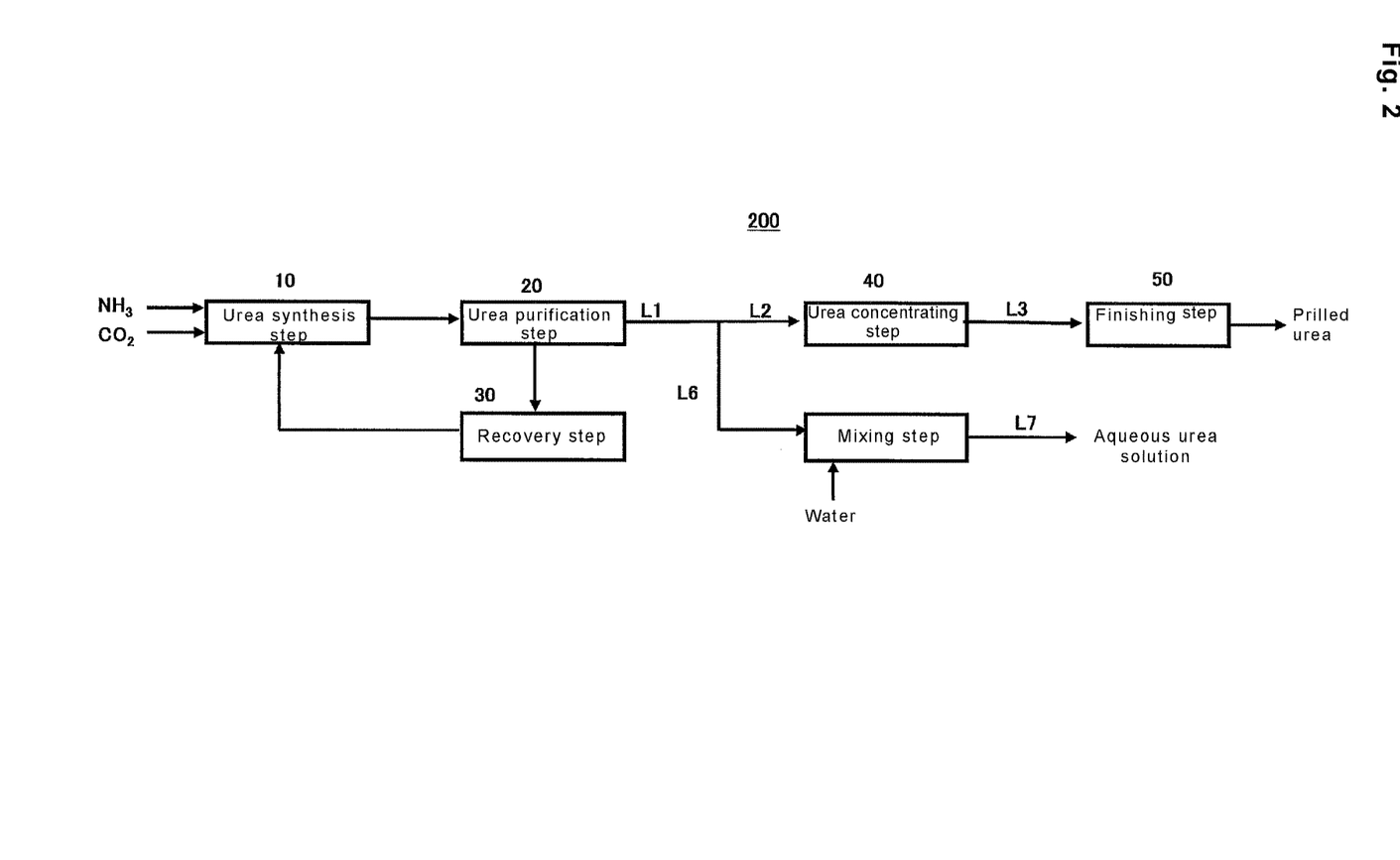
FIG. 2 shows a configuration of a urea production process according to Comparative Example 1.

The urea synthesis step 10 and the urea purification step 20 were operated under the same operation conditions as in Example 1. Further, as shown in FIG. 2, the amount of a solution equal to that in Example 1 was partially drawn (L6) from the aqueous urea solution from the urea purification step 20. When the aqueous urea solution is to be dissolved in water to produce a high-purity aqueous urea solution, 6455 kg/h of water is required. The feed composition of the line L6 (equal to Ls in Example 1) and the composition of an aqueous urea solution (L7) to be produced in the handling are as described below.

TABLE 7

|  |  | L6 | L7 |
|---|---|---|---|
| Urea | Content | 4072 kg/h | ← |
|  | Concentration | 67.37% | 32.58% |
| Biuret | Content | 20 kg/h | ← |
|  | Concentration | 0.33 wt % | 0.16% |
| Ammonia | Content | 33 kg/h | ← |
|  | Concentration | 0.54% | 0.26% |
| Carbon dioxide | Content | 19 kg/h | ← |
|  | Concentration | 0.31% | 0.15% |
| Water | Content | 1901 kg/h | 8366 kg/h |
| Total quantity |  | 6044 kg/h | 12500 kg/h |

From Table 7, the biuret concentration in the aqueous urea solution (L7) produced in this case falls within the standard. However, the solution does not satisfy the standard of reference value of 0.2% (max.) on alkalinity (in terms of ammonia). Accordingly, a step of removing ammonia is required when the aqueous urea solution is utilized. For example, it is possible to produce an aqueous urea solution, in which alkalinity also falls within the standard, by concentrating the solution before dilution with mixture of water.

COMPARATIVE EXAMPLE 2

Figure 3:
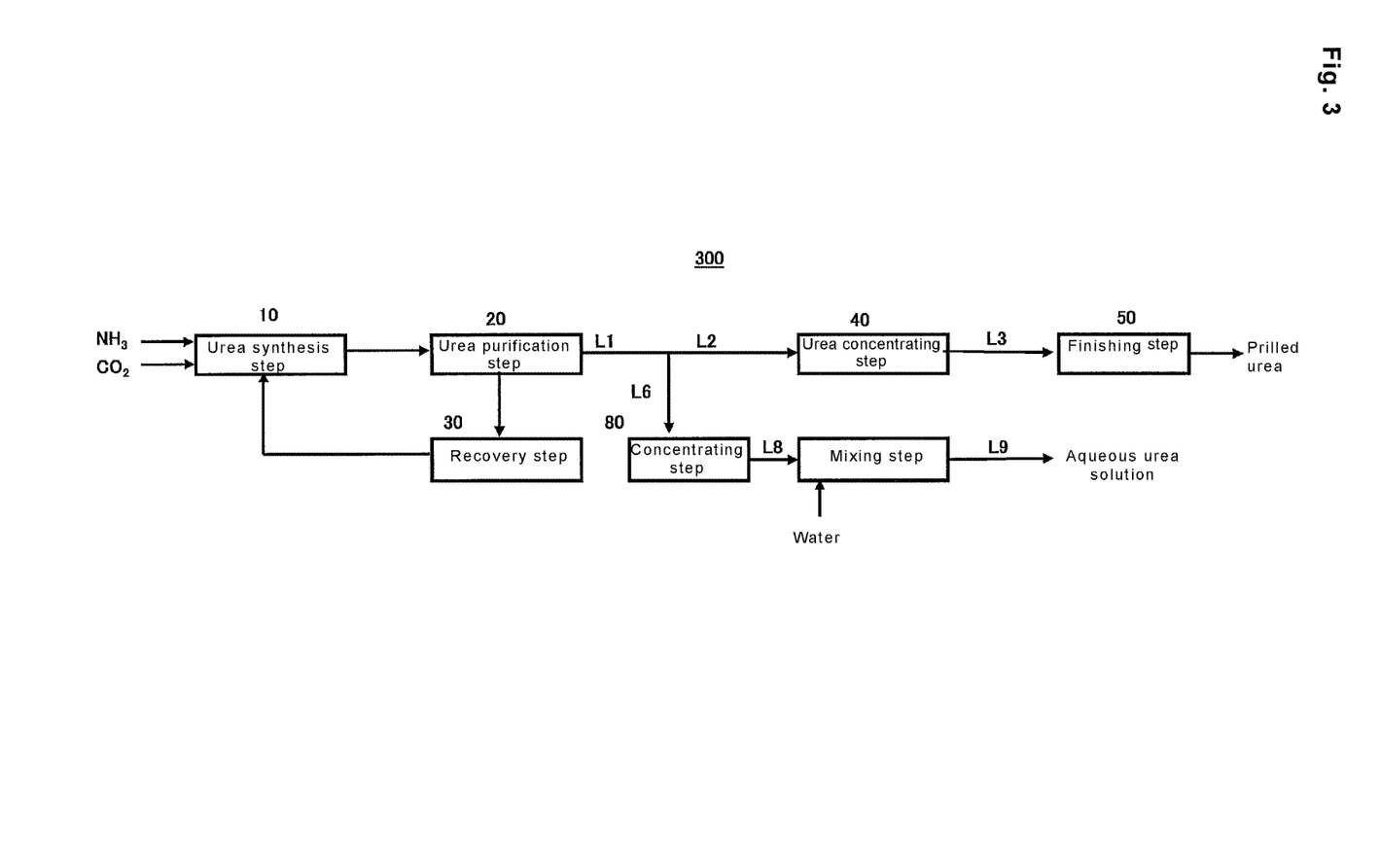
FIG. 3 shows a configuration of a urea production process according to Comparative Examples 2 and 3.

Consequently, as shown in FIG. 3, a urea production plant 300 was examined, which was provided with a concentrating step 80 for concentrating an aqueous urea solution (L6) partially drawn for removing ammonia etc. Operation conditions of the concentrating step are the same as those of the urea concentrating step 40 of the urea production plant in Example 1 or Comparative Example 1. Then, an aqueous urea solution (L8) after concentration was mixed with water to produce a high-purity aqueous urea solution (L9). The compositions of respective solutions at this time are as follows.

TABLE 8

| | | L6 | L8 | L9 |
|---|---|---|---|---|
| Urea | Content | 4087 kg/h | 4072 kg/h | ← |
| | Concentration | 67.45% | 99.00% | 32.58% |
| Biuret | Content | 20 kg/h | 33 kg/h | ← |
| | Concentration | 0.33 wt % | 0.8 wt % | 0.26% |
| Ammonia | Content | 33 kg/h | — | — |
| | Concentration | 0.54% | — | — |
| Carbon dioxide | Content | 19 kg/h | — | — |
| | Concentration | 0.31% | — | — |
| Water | Content | 1901 kg/h | 8 kg/h | 8395 kg/h |
| | Total quantity | 6059 kg/h | 4113 kg/h | 12500 kg/h |

As known from Table 8, the aqueous urea solution (L9) produced in this comparative example has a biuret concentration and alkalinity both falling within the standard. However, the biuret concentration is relatively higher than that in Example 1. This is thought to be due to generation of biuret when the drawn aqueous urea solution was concentrated.

COMPARATIVE EXAMPLE 3

Next, the urea plant 300 in Comparative Example 2 was examined assuming a case where the production volume of prilled urea lowered due to a shortage of a raw material, in the same way as in Example 2. In this comparative example, the aqueous urea solution (L1) from the urea purification step 20 was partially separated (L6) so that the production volume of a high-purity aqueous urea solution was equal to that in Comparative Example 2. Then, the partially drawn aqueous urea solution (L6) was concentrated, and an aqueous urea solution after the concentration (L8) was mixed with water to produce a high-purity aqueous urea solution (L9). Compositions of respective solutions at this time are as follows.

TABLE 9

| | | L6 | L8 | L9 |
|---|---|---|---|---|
| Urea | Content | 4087 kg/h | 4072 kg/h | ← |
| | Concentration | 67.31% | 98.70% | 32.58% |
| Biuret | Content | 32 kg/h | 45 kg/h | ← |
| | Concentration | 0.53% | 1.1 wt % | 0.36% |
| Ammonia | Content | 33 kg/h | — | — |
| | Concentration | 0.54% | — | — |
| Carbon dioxide | Content | 19 kg/h | — | — |
| | Concentration | 0.31% | — | — |
| Water | Content | 1901 kg/h | 9 kg/h | 8383 kg/h |
| | Total quantity | 6072 kg/h | 4126 kg/h | 12500 kg/h |

As known from Table 9, the biuret amount increases due to the lowering of an operation load, and the influence extends into the final aqueous urea solution (L9). That is, the aqueous urea solution has a biuret concentration exceeding the standard value (0.3% by mass, max.), and therefore, cannot be used for an application of an SCR reducing agent. Comparative Examples 2 and 3 are based on a virtual plant having a concentrating step added to the conventional technology (PTL 1) in Comparative Example 1. It can be said that the virtual plant may at least suppress impurities (ammonia etc.) low in an aqueous urea solution. However, it is known that the virtual plant cannot follow the increase in the biuret amount that may be generated due to the change in an operation load.

INDUSTRIAL APPLICABILITY

The present invention is a method for producing a high-purity aqueous urea solution for an SCR reducing agent, using, as a raw material, a urea-containing solution from a urea synthesis step or a urea purification step in a urea production plant. According to the present invention, a high-purity aqueous urea solution within the standard (biuret concentration: 0.3% by mass, max.) can be produced, regardless of a biuret concentration in the urea-containing solution to be received.

The invention claimed is:
1. A method for producing a high-purity aqueous urea solution in a urea production process, the process comprising the steps of
   (a) synthesizing urea from a raw material feed to produce a urea synthesis liquid,
   (b) purifying the urea synthesis liquid to produce an aqueous urea solution having high urea concentration,
   (c) separating a part of the urea synthesis liquid and/or a part of the aqueous urea solution in or after step (b),
      (c1) crystallizing urea contained in the separated urea synthesis liquid and/or aqueous urea solution of step (c) to produce crystal urea being a solid; and
      (c2) mixing the crystal urea produced in step (c1) with water to produce a high-purity aqueous urea solution,
   (d) concentrating urea in the aqueous urea solution produced from step (b) that is unseparated in step (c), and
   (e) producing solid granular urea from the concentrated urea produced in step (d).
2. The method for producing a high-purity aqueous urea solution according to claim 1, further comprising a urea recovery step of receiving ammonia and carbon dioxide separated in step (b), wherein step (c1) comprises the steps of:
   crystallizing the urea to produce slurry containing crystal urea;
   subjecting the slurry containing crystal urea to solid-liquid separation;
   separating the subjected slurry containing crystal urea into crystal urea and a mother liquid; and further optionally sending back a part of the mother liquid separated from the slurry containing crystal urea to step (a) through said urea recovery step.
3. The method for producing a high-purity aqueous urea solution according to claim 1, wherein conditions for step (c1) are 60 to 80 mmHg (abs) in pressure and 50 to 80° C. in temperature.
4. The method for producing a high-purity aqueous urea solution according to claim 1, wherein:
   the urea production process further comprises separating a part of the aqueous urea solution in step (d), and wherein step (c1) further comprises crystallizing urea contained in said separated part of the aqueous urea solution in step (d).
5. The method for producing a high-purity aqueous urea solution according to claim 2, wherein conditions for step (c1) are 60 to 80 mmHg (abs) in pressure and 50 to 80° C. in temperature.

6. The method for producing a high-purity aqueous urea solution according to claim 2, wherein:
the urea production process further comprises separating a part of the aqueous urea solution in step (d), and wherein step (c1) further comprises crystallizing urea contained in said separated part of the aqueous urea solution in step (d).

7. The method for producing a high-purity aqueous urea solution according to claim 3, wherein:
the urea production process further comprises separating a part of the aqueous urea solution in step (d), and wherein step (c1) further comprises crystallizing urea contained in said separated part of the aqueous urea solution in step (d).

* * * * *